United States Patent [19]

Flatau

[11] 4,284,194
[45] Aug. 18, 1981

[54] PACKAGE FOR A MULTIPLE OF STERILE SUTURES WITH OR WITHOUT NEEDLES ATTACHED

[75] Inventor: Alison Flatau, Boulder, Colo.

[73] Assignee: American Cyanamid Company, Stamford, Conn.

[21] Appl. No.: 19,386

[22] Filed: Mar. 12, 1979

[51] Int. Cl.³ ............................................. A61B 17/06
[52] U.S. Cl. ................................ 206/63.3; 128/335.5; 206/484; 229/87 R
[58] Field of Search ................... 206/63.3, 388, 484, 206/484.2; 229/87 R; 128/335.5

[56] References Cited

U.S. PATENT DOCUMENTS

| | | | |
|---|---|---|---|
| 3,280,971 | 10/1966 | Regan | 206/63.3 |
| 3,363,751 | 1/1968 | Shave et al. | 206/63.3 |
| 3,487,917 | 1/1970 | Shave et al. | 206/63.3 |
| 3,647,057 | 3/1972 | Ashmead et al. | 206/17 |
| 4,089,409 | 5/1978 | Cerwin | 206/63.3 |
| 4,089,410 | 5/1978 | Bolanowski et al. | 206/63.3 |
| 4,121,711 | 10/1978 | Bolanowski | 206/63.3 |
| 4,126,221 | 11/1978 | Cerwin | 206/63.3 |

FOREIGN PATENT DOCUMENTS

| | | | |
|---|---|---|---|
| 148119 | 1/1951 | Australia | 206/63.3 |
| 2754936 | 6/1978 | Fed. Rep. of Germany | |
| 453345 | 9/1936 | United Kingdom | |

*Primary Examiner*—F. J. Bartuska
*Attorney, Agent, or Firm*—Charles F. Costello, Jr.

[57] ABSTRACT

A single dispensing surgical suture package containing multiple surgical suture strands is disclosed. The package comprises a panel which has a back, a strand cover flap adjacent and connected to one side of the panel by at least one score line, and a foam layer contained on coordinating surfaces of the panel and the flap. The package also comprises an outer panel containing the panel described above.

11 Claims, 12 Drawing Figures

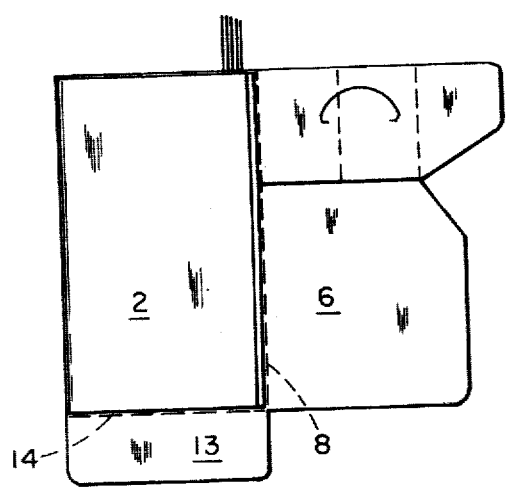
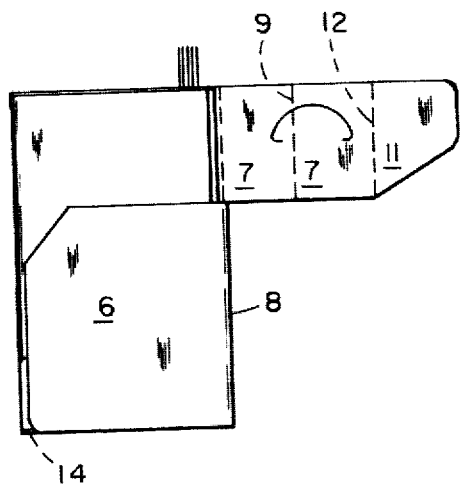
FIG.4a
FIG.4b
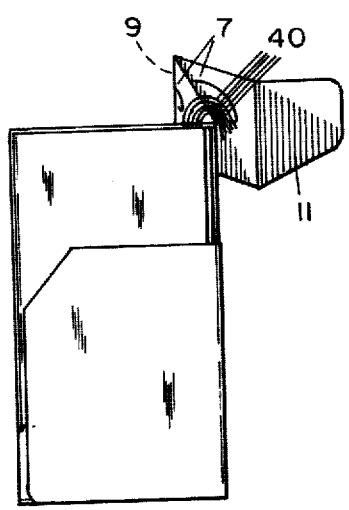
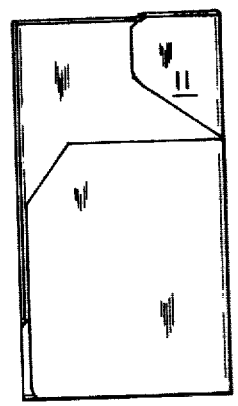
FIG.4c
FIG.4d

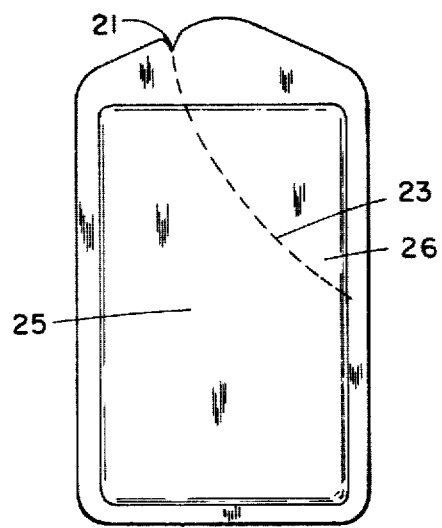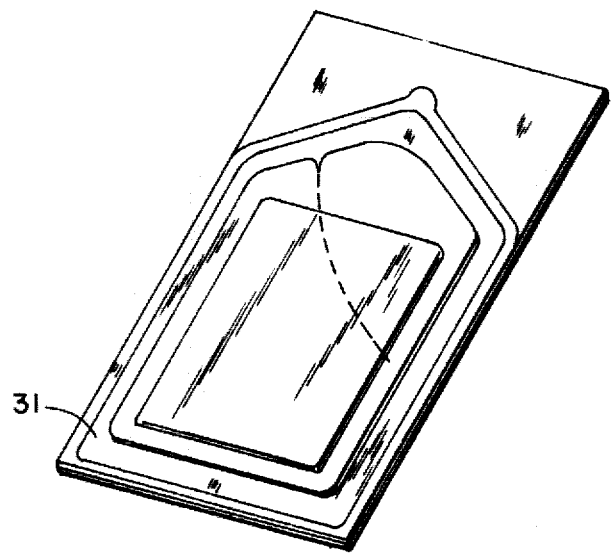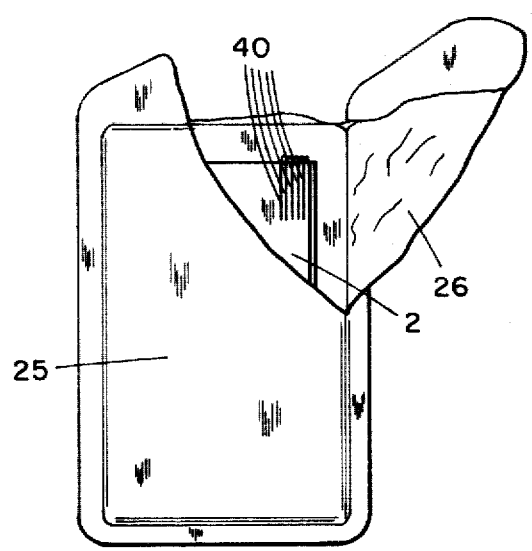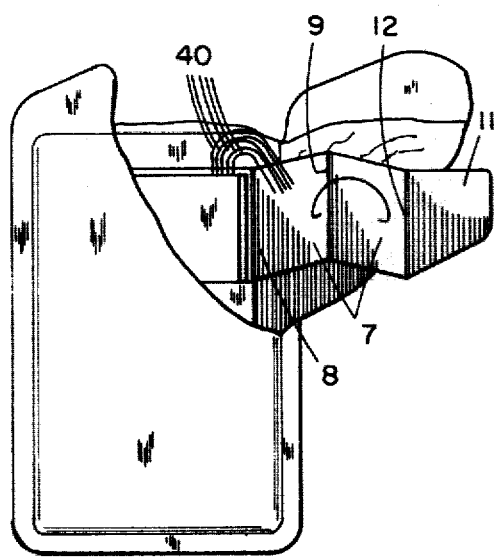

PACKAGE FOR A MULTIPLE OF STERILE SUTURES WITH OR WITHOUT NEEDLES ATTACHED

BACKGROUND OF THE INVENTION

This invention relates to a single dispensing surgical package containing multiple surgical suture strands.

The direct dispensing of a single surgical suture from a suture package is disclosed in U.S. Pat. No. 4,089,410. The direct dispensing of multiple surgical sutures from a suture package is disclosed in U.S. Pat. No. 4,121,711. These direct dispensing packages can contain either needled or non-needled sutures. These packages are great advances in the surgical suture packaging art.

It became apparent, however, that a greater need in the art is a package containing multiple surgical suture strands, either needled or non-needled, from which a single suture is directly dispensed. The suture package of this invention solves this need.

The Applicant is not aware of any prior art which, in her respective judgement as a person skilled in the suture packaging art, would anticipate or render obvious the package of this invention. However, to fully develop the background of the invention, or establish the state of the art, the following references are disclosed.

U.S. Pat. No. 4,089,409 describes winding pins to maintain multiple surgical suture strands in a suture package until the package is positioned as retaining means for the strands. U.S. Pat. No. 3,280,971 and German Offen. No. 2,754,936 describe, respectively, a retaining tube in a suture package, and retaining means on a sheet, to maintain multiple surgical suture strands in a suture package.

Also, U.S. Pat. Nos. 3,487,917 and 3,363,571; and Great Britain Pat. No. 453,345 describe a single surgical suture strand contained in a suture package in a "zig-zag" or sinusoidal configuration. Finally, U.S. Pat. No. 3,647,057 describes foam as a frictional material for packaging and for individual dispensing of needles in a package. All of the prior art described above is incorporated herein by reference.

The single dispensing surgical suture package of this invention has advantages over the prior art. One advantage is that the surgical suture strands of this invention are contained on a foam layer. Thus, means to retain the strands in the package are eliminated. Another advantage is that overlapping of the suture strands, in the concave and convex portions of the sinusoidal configuration, can occur during loading without impairing the dispensing of a single surgical suture.

Still another advantage is that the inner envelope and label of this invention remains in one piece after opening. The proliferation of packaging materials within the immediate area of the surgical operation or other surgical procedure is therefore reduced.

The suture package of this invention can contain a multiple of identical sutures. The package can also contain a combination of different needles and/or sutures which can be identified, e.g. by color, for different surgical procedures.

SUMMARY OF THE INVENTION

A single dispensing surgical suture package containing multiple surgical suture strands has now been invented. In one embodiment, the package comprises a label which has a back panel;

a strand cover flap adjacent and connected to one side of the panel by at least one score line;

a foam layer contained on coordinating surfaces of the panel and the flap;

at least two surgical suture strands contained on the foam layer of the panel in a sinusoidal configuration, with the flap folded along the score line onto the strands and with one end of the strand external to the panel and the flap. A single suture can then be grasped and directly dispensed from the package. The package described above containing braided sutures is preferred. The package described above containing from about five to twelve surgical suture strands is also preferred. Finally, the package described above wherein the ends of the strands external to the panel and the flap ae needled is in another embodiment.

The package described above wherein the label has attachment means for holding the flap onto the panel is within the scope of this invention.

An improved single surgical suture dispensing package consisting of a sealed envelope having a tearing notch and a tear angle guideline enclosing a label containing multiple surgical suture strands is also within the scope of this invention. The improvement comprises the direct dispensing label described above in which the ends of the surgical suture strands external to the panel and the flap of the label are adjacent to the tear angle guideline of the envelope, such that when the envelope is opened, the ends of the strands are exposed. A double envelope single surgical suture dispensing package consisting of a strippable outer envelope containing the sealed envelope described above is preferred.

In an alternative embodiment, the single surgical suture strands of this invention comprises an outer label and an inner label.

The outer label has a back panel;

an upper side flap adjacent and connected to the back panel by at least one score line, and containing either a score line or a retention slit, for retaining the ends of the surgical suture strands;

a tab adjacent and connected to the upper side flap by at least one score line, and opposite the back panel, for dispensing the ends of the strands;

a lower side cover flap adjacent the back panel and the upper flap, and connected to the back panel by at least one score line;

a bottom flap adjacent the back panel and the lower side cover flap, and connected to the panel by at least one score line.

The inner label has a back panel;

a strand cover flap adjacent and connected to one side of the inner label back panel by at least one score line;

a foam layer contained on coordinating surfaces of the inner label back panel and the strand cover flap;

at least two surgical suture strands contained on the foam layer of the panel with a sinusoidal configuration; with the flap folded along the score line onto the strands and with one end of the strands external to the inner label back panel and the strand cover flap.

The inner label is contained within the outer label by the following sequence. The inner label back panel is laid onto the outer label back panel with one end of the strands adjacent to and retained by the outer label upper side flap. The outer label bottom flap is folded onto the inner label cover flap. The outer label lower flap is then folded onto the bottom flap. The outer label upper side flap is then folded onto the outer label back panel, and the outer label tab is folded onto the outer label back panel or onto the outer label upper flap. When the tab is lifted, a single suture can then be grasped and directly dispensed from the package. The above described alternative embodiment containing braided sutures is preferred. The package in the above described alternative embodiment containing from about five to twelve surgical suture strands is also preferred. Finally, the package in the above described alternative embodiment wherein the ends of the strands external to the inner label back panel and the strand cover flap are needled is another embodiment.

Attachment means for holding the outer label lower side cover flap onto the outer label back panel is within the scope of this invention. For example, an attachment means having at least one locking slit on coordinating edges of the lower side cover flap and the outer label back panel can be used.

An improved single dispensing surgical suture package consisting of a sealed envelope having a tearing notch and a tear angle guideline enclosing an outer label, and an inner label, and an inner label containing multiple surgical suture strands is also within the scope of this invention. The improvement comprises the direct dispensing outer and inner labels, acting in coordination, described in the above alternative embodiment in which the tab of the outer label is adjacent to the tear angle guideline of the envelope, such that when the envelope is opened and the tab is lifted, the ends of the strands are exposed. A double envelope single dispensing surgical suture package consisting of a strippable outer envelope containing the sealed envelope described above is preferred.

BRIEF DESCRIPTION OF THE DRAWINGS

FIGS. 4a to 4d describe the folding of the label of FIG. 1 onto the label of FIG. 3;

FIG. 5 is an inner envelope containing the labels of FIGS. 1 or 4d;

FIG. 6 is an outer envelope containing the envelope of FIG. 5;

FIGS. 7 and 8 show the direct dispensing of sutures from the labels of FIGS. 2 and 4c, respectively, contained in the inner envelope of FIG. 5.

DESCRIPTION OF THE INVENTION

Figure 1:
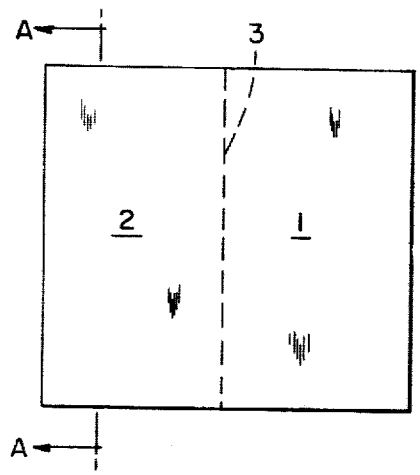
FIGS. 1 and 3 are front views of the inner and outer suture label, respectively.
Figure 1A:
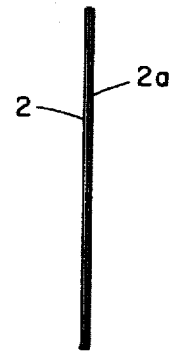
FIG. 1a is a section view along the line A—A of FIG. 1.

FIG. 1 describes the inner suture label. This label can be cutout and scored from a sheet of sterilizable stock, e.g., surgical grade kraft paper. The inner label comprises a back panel 1 and a strand cover flap 2. The flap 2 is connected to the panel 1 by a score line 3. FIG. 1a is a section view along the line A—A of FIG. 1 and describes the foam layer 2a attached to the label. The foam layer is contained on coordinating surfaces of the flap 2 and back panel 1.

Figure 3:
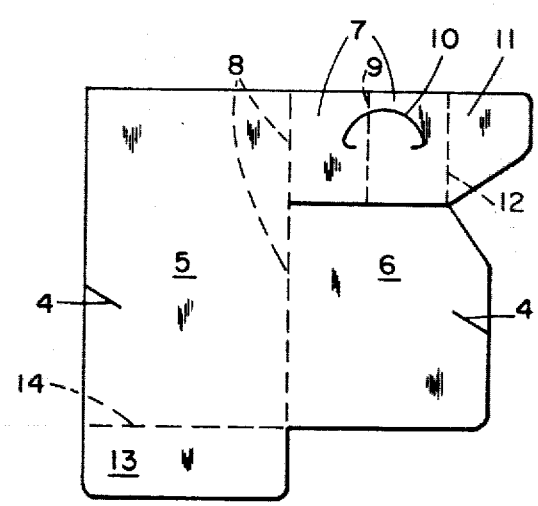

FIG. 3 describes the outer suture label. This label can be cutout and scored from a sheet of sterilizable stock, e.g., surgical grade kraft paper. The paper can be coated with polyethylene for heat sealing. The first part of the label consists of a back panel 5 to which is attached by score line 8 a lower side cover flap 6 and an upper side flap 7. Optional score line 9 can separate the end-flap 7 into two parts. The end flap when folded into two parts along score line 9 is used to contain the ends of needled or non-needled sutures. Optional slit 10 can hold the ends of non-needled sutures. Score line 9 and slit 10 are alternative optional embodiments and are therefore not used together. The suture dispensing tab 11 is attached to the upper side flap 7 by score line 12. Bottom flap 13 is attached to the back panel 5 by score line 14.

In FIG. 3 locking slits 4 hold the lower side cover flap 6 back panel 5. Although locking slits are described, other attachment means, e.g., spot bonding, heat sealing or a coordinating tab and groove can be used on the periphery of the labels of FIGS. 1 and 3.

Figure 2:
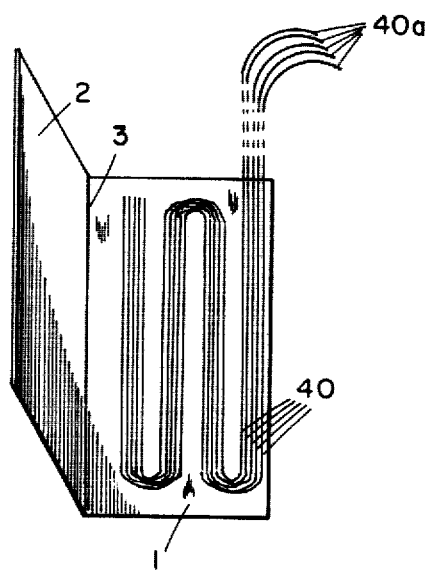
FIG. 2 describes the sinusoidal loading configurations for the label of FIG. 1.

FIG. 2 describes the sinusoidal loading configuration of the suture strands 40 onto the label of FIG. 1. The ends of the suture strands 40 can optionally contain needles 40a.

The loading of the sutures onto the label can be by means known in the art, e.g. as disclosed in Germ. Offen. No. 2,754,936. The cover flap 2 is folded onto the back panel 1 along score line 3. The suture strand ends 40 or 40a are then folded over the cover flap 2. FIG. 7 describes the orientation of the inner label of FIG. 2 in the inner envelope of FIG. 5.

The inner label (which is also termed the sleeve or cover) of FIG. 2 presents the ends of the sutures for dispensing.

Critical to this invention is the surface of the inner suture label. It is the foam that provides the friction for the single suture dispensing. The foam must be of a thickness and/or cellular size to maintain a high coefficient of static friction. The foam Microfoam ® XSP-1 (E. I. DuPont Co., Wilmington, Del., U.S.A.) having a thickness of 1/32 inch is useful for this purpose. Although foam is preferred any low slip material, e.g. embossed paper, can be used to maintain a sufficiently high coefficient of static friction. The following theory, although not a part of this invention, is disclosed as one explanation for the single suture dispensing package. Static friction is greater than sliding (moving) friction. The force initially introduced to a single suture for dispensing, e.g., by pulling the suture with the thumb and index finger, is large enough to overcome the static friction of that one suture against the foam and the other sutures. However, that one suture's sliding friction is not large enough to overcome the static friction of the other sutures against the foam and against each other. Thus multiple surgical suture strands can be packaged together and directly dispensed singly without tangling.

The attachment means of the foam to the inner label can be by lamination e.g., with an adhesive, or by other bonding means and is not critical to the practice of this invention.

The label is useful for singly dispensing non-needled multiple sutures or single armed (that is, one needle at one end of a suture strand) needled multiple sutures. Within the scope of this invention is a label containing up to twelve surgical suture strands. From about five to twelve surgical suture strands are preferred. Braided surgical sutures are also preferred because they most accomodate the sinusoidal configuration. Also within the scope of this invention are suture lengths of up to 36 inches. A suture length of between about 18 inches and 27 inches is preferred. It is to be understood that the preferred number and lengths of surgical suture strands is based on conventional suture package sizes. However, more and longer surgical suture strands may be contained in the package by increasing the package size.

FIGS. 4a to 4d teach the proper folding of the outer suture label around the inner suture label of FIG. 2. The inner back panel 1 (shown in FIG. 2) is laid onto the outer back panel 5 (Shown in FIG. 3). Referring to FIGS. 4a and 4b, the bottom flap 13 and then the cover flap 6 are folded along score lines 14 and 8, respectively, onto the inner cover flap 2. The bottom flap 13 holds the label of FIG. 1 on the outer label during loading into the inner envelope of FIG. 5. The suture strand ends 40 (or 40a) and the upper side flap 7 are now approximately adjacent to each other.

Referring to FIG. 4c and 4d, the upper side flap 7 is folded along score line 9. The suture strand ends 40 (or 40a) are then taken over the top of the outer back panel 5 (as shown in FIG. 3) and placed in the "pocket" formed by the folded flap 7. The upper side flap 7 is then folded onto itself along score line 9 and then onto the outer back panel 5 along score line 8 (shown in FIG. 4b).

The suture dispensing tab 11 is then folded onto the strand cover flap 2 along score line 12 (shown in FIG. 4b). FIG. 8 describes the orientation of the label of FIG. 4d in the inner envelope of FIG. 5.

In an alternative embodiment, the upper side flap 7 contains retention slit 10 (shown in FIG. 3) Score line 9 is either removed or not used. The suture strands ends 40 are placed in the retention slit 10. The upper side flap 7 is then folded onto the strand cover flap 2 along score line 8 shown in FIG. 3. The suture dispensing tab 11 is then folded onto the upper side flap 7 along score line 12.

In FIG. 6, the outer envelope 31 is peeled off and the inner envelope of FIG. 5 is obtained. In FIG. 5, using the tearing notch 21 as a start, the user opens the inner envelope 25 by tearing along the dotted guideline 23 without detaching the torn portion 26. To aid the user, a tear arrow could be placed on the dotted guideline 23.

FIGS. 7 and 8 show the availability of the suture strand ends 40 (or 40a) and of the suture dispensing tab 11, respectively, after the inner envelope 25 has been torn. In FIG. 8, when non-needled sutures are used, the non-needled ends tend to "pop up" when the inner envelope of FIG. 5 is torn open and the tab is lifted. The torn portion 26 is not detached from the envelope. The direct dispensing of non-needled sutures from the package of this invention, according to good surgical practice, is by hand. The direct dispensing of needled sutures from the package of this invention, according to good surgical practice, is by hand or with a needle holder.

In FIGS. 7 and 8, because of the design characteristics, the label of FIG. 2 and 4d is securely locked within the opened portion of the envelope 25 during direct dispensing and the entire package remains intact. Thus no additional materials, other than the dispensed suture strand, is added to the operating area. Related hazards are thus minimized and accountability is simplified.

I claim:

1. A single dispensing surgical suture package containing multiple surgical suture strands which comprises
an outer label having:
a back panel;
an upper side flap adjacent and connected to said panel by at least one score line, and containing means for retaining the ends of said surgical suture strands;
a tab adjacent and connected to said upper flap by at least one score line, and opposite said panel, for exposing the ends of said strands;
a lower side cover flap adjacent said panel and said upper flap, and connected to said panel by at least one score line;
a bottom flap adjacent said panel and said lower flap and connected to said panel by at least one score line; and
an inner label having:
a back panel;
a strand cover flap adjacent and connected to one side of said inner label back panel by at least one score line;
a foam layer contained on coordinating surfaces of said inner label back panel and said strand cover flap;
at least two surgical suture strands contained on the foam layer in a sinusoidal configuration, with said strand cover flap folded along said score line onto said strands and with one end of said strands external to said inner label back panel and said strand cover flap;
whereby said inner label back panel is laid onto said outer label back panel with one end of said strands adjacent to and retained by said outer label upper side flap, said outer label bottom flap is folded onto said inner label cover flap, said outer label lower flap is folded onto said bottom flap, said outer label upper side flap is folded onto said outer label back panel or said inner label strand cover flaps, and said outer label tab is folded onto said outer label back panel or said outer label upper flap;
such that when said tab is lifted, a single suture can be grasped and directly dispensed from said package.

2. A package of claim 1 wherein the containing means is a score line.

3. A package of claim 1 wherein the containing means is a retention slit.

4. A package of claim 2 or 3 containing braided surgical suture strands.

5. A package of claim 2 or 3 containing from about five to twelve surgical suture strands.

6. A package of claim 1 wherein the ends of the strands external to the inner label back panel and the strand cover flap are needled.

7. A package of claim 1 wherein the outer label has attachment means for holding the lower side cover flap onto the panel.

8. A package of claim 7 wherein the attachment means is at least one locking slit on coordinating edges of the flap and the panel.

9. A package of claim 1 wherein the inner label has attachment means for holding the strand cover flap onto the inner label back panel.

10. A single dispensing surgical suture package consisting of a sealed envelope having a tearing notch and a tear angle guideline enclosing an outer label, and an inner label containing multiple surgical suture strands, the improvement wherein said outer and inner labels, in coordination, are the direct dispensing labels of claim 1 or 2 or 3 in which the tab of the outer label is adjacent to the tear angle guideline of said envelope, such that when said envelope is opened and said tab is lifted, the ends of said strands are exposed.

11. A double envelope single surgical suture dispensing package consisting of a strippable outer envelope containing a sealed envelope of claim 10.

* * * * *